(12) United States Patent
Henkin et al.

(10) Patent No.: US 6,251,080 B1
(45) Date of Patent: Jun. 26, 2001

(54) SELF CONTAINED AMBULATORY BLOOD PRESSURE CINCTURE

(75) Inventors: Raphael Henkin, Monarch Beach; Edward J. Crespin, San Marcos, both of CA (US)

(73) Assignee: Del Mar Medical Systems, LLC, Irvine, CA (US)

( * ) Notice: Subject to any disclaimer, the term of this patent is extended or adjusted under 35 U.S.C. 154(b) by 0 days.

(21) Appl. No.: 09/311,664

(22) Filed: May 13, 1999

(51) Int. Cl.⁷ ........................................................ A61B 5/00
(52) U.S. Cl. ........................ 600/490; 600/493; 600/494; 600/500
(58) Field of Search .................................. 600/485, 490, 600/493–6, 500

(56) References Cited

U.S. PATENT DOCUMENTS

| | | | |
|---|---|---|---|
| 2,841,149 | 7/1958 | Tourniquet | 128/327 |
| 4,175,562 | 11/1979 | Honan | 128/303 |
| 4,353,374 | 10/1982 | Klaus | 128/686 |
| 4,535,783 | 8/1985 | Morangoni | 128/711 |
| 4,549,550 | * 10/1985 | Kami | 600/499 |
| 4,890,625 | 1/1990 | Sorense | 128/680 |
| 4,896,676 | * 1/1990 | Sasaki | 600/494 |
| 4,898,180 | * 2/1990 | Farrelly | 600/494 |
| 4,966,155 | 10/1990 | Jackson | 128/671 |
| 5,107,848 | 4/1992 | Oku | 128/686 |
| 5,121,954 | 6/1992 | Holtsch | 292/318 |
| 5,218,966 | 6/1993 | Yamasawa | 128/677 |
| 5,341,694 | 8/1994 | Kaplan | 128/672 |
| 5,421,341 | 6/1995 | Morangoni | 128/677 |
| 5,447,160 | 9/1995 | Kankkunen | 128/677 |
| 5,485,848 | 1/1996 | Jackson | 128/672 |
| 5,687,732 | * 11/1997 | Inagaki et al. | 600/485 |
| 5,692,513 | * 12/1997 | Davis et al. | 600/499 |

FOREIGN PATENT DOCUMENTS

95/00074 * 1/1995 (WO) ................................ 600/485

* cited by examiner

*Primary Examiner*—Robert L. Nasser
(74) *Attorney, Agent, or Firm*—W. D. English, III

(57) ABSTRACT

A long term ambulatory blood pressure monitor is disclosed in which all elements of the monitor are compactly and inconspicuously contained in/on a cincture housing mounted on an inflatable arm band fixedly and comfortably positioned on the patient arm. System control and display modules are efficiently placed in a flip top mode on the cincture housing itself and alternatively in a wrist watch mode on the patient wrist. Non volatile EEPROM blood pressure data memory is disposed adjacent EPROM system memory and microprocessor controller circuitry on a compact PCB within the cincture housing along with pneumatic motor/pump and solenoid for inflation/deflation of the arm band to obtain systolic/diastolic blood pressure readings via the oscillatory detection method.

1 Claim, 17 Drawing Sheets

SELF CONTAINED AMBULATORY BLOOD PRESSURE CINCTURE

BACKGROUND OF THE INVENTION

1. Field of the Invention

The invention lies in the general field of noninvasive, ambulatory blood pressure measurement equipment. More specifically, the invention relates to an ambulatory, long term blood pressure monitoring system, where essentially all of the equipment components are mounted on the arm band that is conventionally used in existing blood pressure detecting systems.

2. Description of the Prior Art

Various methods have been utilized in the past for accurate blood pressure determination with the most common being a "tourniquet" type arm band with overlapping Velcro attachments applied around the biceps/triceps muscle area of the arm. The band would typically be constructed with an inflatable air bladder therein with a hand operated rubber bulb pump distally connected thereto via a lengthy air hose. The band would be initially tightened by increasing air pressure to a predetermined level to completely stop the flow of blood through the arm. Using the auscultatory method to listen for Karotcoff (K) sounds (bubbling blood squeezing through a compressed artery), a microphone or stethoscope would be applied to the arm over the brachial artery, immediately adjacent the arm band. The air pressure in the arm band would then be slowly released by a hand operated air release valve until the first K sound, the systolic, would be heard, i.e. the sound of blood initially bubbling through the artery. The fourth or fifth K sound, the diastolic, would follow in time as the arm band pressure is further released and as the blood, no longer constricted from flow, freely flows though the artery without bubbling. By such means, the systolic/diastolic blood pressure, typically being 120/80, and variations thereof, as well as the pulse rate, typically 60 beats/minute, could conveniently be determined.

More recent methods of implementing the foregoing blood pressure measurement have been devised to operate in a long term ambulatory environment by using a similar inflatable arm band with a lengthy air hose and electrical lead extending therefrom and attached to a magnetic tape recorder, usually mounted on a waist belt of the patient. A relatively large recorder enclosure/housing, containing not only the blood pressure data recording medium, i.e. magnetic tape reels, but also carried a pneumatic (air) pump and motor to inflate the air bladder, along with a printed circuit board for a microprocessor and appropriate electronics to accurately record periodic blood pressure events or specific event prompted blood pressure samples, and Liquid Crystal Display (LCD) screen with necessary control buttons (keyboard) for event marking or system control. A microphone would be attached by tape to the patient's arm under the inflatable arm band, with a lengthy electronic lead to the recorder housing to provide periodic blood pressure events to be recorded for later evaluation.

Several such prior art devices, elements and systems are illustrated in the following U.S. Pat. No. 5,485,848 (Jackson) describes a continuous blood pressure monitoring device mounted in a wrist watch fashion to detect systolic and diastolic pressure readings taken at the wearer's wrist and calibrates said readings in relation to a conventional upper arm cuff mounted sphygmomanometer device coupled by a conventional lengthy air tube to an air pump and appropriate electronics, central processor unit (CPU) and a stored calibration table. Such wrist mounted blood pressure sensing devices are not, however, usually taken at the same level as the heart of the patient which tends to yield inaccurate pressure variations, and furthermore, blood flowing through smaller arteries on the wrist do not yield the strong signature that can be found in the large brachial artery of the upper arm. Another U.S. Pat. No. 5,447,160 (Kankkunen) discloses a method for restricting the air pressure in the conventional upper arm cuff. Another prior art disclosure in U.S. Pat. No. 5 5,141,341 (Marangoni) discloses an ambulatory blood pressure device wherein the air pump, inflating valve and pressure transducer are all located in the arm mounted cuff. In yet another U.S. Pat. No. 5,351,694 (Davis), an adjustable, non inflatable arm band/cuff is applied to a limb to pick up blood pressure measurements and send the accumulated information by electrical lead, wireless, and optical transmission means for further analysis. U.S. Pat. No. 4,353,374 (Rebbe) disclosed a unique blood pressure band having a weighted buckle attached to an end of the band through which the other band end is passed through, forming a loop that tightens the band to an arm. Magnetic or other similar attaching means holds the band and loop in position. U.S. Pat. No. 5,218,966 (Yamasawa) teaches application of a photo electric sensor in a finger band to detect blood pressure. Yet another U.S. Pat. No. 5,121,954 (Holtsch) relates to a unique connecting means for forming an arm band, wherein a pin with inclined surfaces applied to a pair of transverse grooves is utilized to lock an arm band in position. U.S. Pat. No. 1,107,848 (Oku), discloses a non mobile blood pressure device wherein a cylindrical collar situated in a casing serves as an arm band and is adjusted by a sliding member coupled to a spring mounted knob. In U.S. Pat. No. 4,966,155 (Jackson), a waist mounted physiological monitor incorporates an electroconductive elastomeric means the resistance value of which changes as a function of the elongation of the elastic belt. U.S. Pat. No. 4,890,625 discloses a blood pressure cuff having an internal acoustic pickup coupled via a lengthy pneumatic tube to a first and second enclosures for converting acoustic signals to electrical signals.

The invention disclosed herein improves on the foregoing prior art blood pressure apparatus by encompassing a fully self contained blood pressure package on the cuff of the blood pressure inflatable arm band, and by such means, substantially shortening the air tube between air pump and air bladder, which in turn, dramatically increases system efficiency and decreases energy consumption, i.e. battery power. The lengthy tube of prior art pumps tended to waste battery power to run the electric motor of the air pump because much more pressure was required to pump a lengthy compressible volume of air along the lengthy air tube from the pump in the recorder mounted on the patient's waist up to the arm band to inflate the air bladder. The invention disclosed herein mounts the air pump, electric motor and all electronic components "on the arm band"; as a result, there is no lengthy pneumatic (air) hose and related volume of air to compress; therefor, there is no waste of energy in compressing air as with prior art. Additional problems are also eliminated by eliminating the lengthy air hose. There is frequently problems with the a "kinked" air hose especially during periods of sleep as the patient wearing the monitor roles over in bed; such a kinked/blocked off air hose invariably leads to inaccurate if not completely erroneous readings.

In addition, the invention herein further improves on the prior art by using the oscillatory method of blood pressure measurement; i.e. detecting variable air pressure changes or "pressure blips" to indicate the respective systolic/diastolic pressure measurements. The variable pressure measurement is made by an oscillametric sensor also mounted "in the arm band"; i.e. there is no longer any need to tape a microphone to the patient's arm as with existing art.

The invention herein further improves on the prior art in that, because the data recording means, also mounted in the arm band cincture housing, isn't the bulky and mechanically complex magnetic tape reels of prior art, but is instead a very compact and highly reliable digital integrated circuit technology (EEPROM) and the system display and control mechanism may now be confined to a very small housing that can conveniently be mounted in a device similar to a wrist watch or in a flip top module positioned on the arm band cincture housing instead of being mounted on a patient belt. The substantially smaller data recorder housing not only provides increased reliability but also much greater patient flexibility in mounting and accessing the recorder device.

The invention improves on the prior art in yet another manner in that the cincture housing for enclosure of all the ambulatory blood pressure detector equipment effects a much more convenient arm band mechanism that can be mounted by the patient alone with only one hand. The inconvenient Velcro attachment means of existing blood pressure systems often encounters difficulty in adjusting the arm band to varying sized patient arms in different surroundings, and requires at least two hands to mount. In addition, presently used Velcro type arm bands tend to incur slippage which in turn creates noise leading to numerous false readings.

Applicant's invention overcomes all the foregoing limitations of the prior art a solves a long standing need for a non obtrusive, non visual, non invasive, compact, hidden, and reliable ambulatory blood pressure recorder.

SUMMARY OF THE INVENTION

The invention is a long term, ambulatory blood pressure monitor that consists of an inflatable arm band for mounting around the upper arm of a patient with a very short inflation pneumatic air tube. The arm band is coupled together by a cincture device that can be mounted and attached by the patient with only one hand and that contains within itself all components necessary for the monitoring process, including the microprocessor controller and system memory (EPROM), non volatile digital data memory (EEPROM) and printed circuit board, the pneumatic air pump and motor, the air flow shut off solenoid and bleed valve, the battery power supply, and the oscillatory blood pressure sensor. An LCD (display) and function control module is coupled to the cincture device by an electrical lead from a wrist mounted module and alternatively from a flip top module mounted directly on the cincture.

OBJECTS OF THE INVENTION

It is a primary object of the invention to provide an ambulatory, long term blood pressure monitor that is a single, compact unit that can be inconspicuously worn and operated out of sight and under clothing.

Another object of the invention is to make an ambulatory blood pressure monitor that does not need lengthy pneumatic air tubes or electrical leads.

Yet another object of the invention is to lengthen the monitoring period by diminishing the power drain by substantially shortening the pneumatic air tube between the pneumatic air pump and the inflatable air bladder and by changing prior art magnetic tape drives to solid state digital memory.

Another object is to utilize digital printed circuit, non volatile memory to diminish not only data memory physical size, but also to diminish artifact, and energy consumption.

Another object of the invention is to provide a Blood Pressure monitor in which a patient can easily and conveniently access and press an event button, initiate a reading process, and visually ascertain the blood pressure and rate reading at any time and in an inconspicuous manner.

Yet another object of the invention is to provide a BP monitor that periodically takes a Blood Pressure sample in an inconspicuous manner whilst being hidden under clothing.

DETAILED DESCRIPTION OF A PREFERRED EMBODIMENT

Prior art ambulatory blood pressure equipment consisted of an elastic or flexible arm band having an inflatable air bladder disposed therein, and a blood pressure monitor/recorder housing adapted to be worn on a belt around the waste of an ambulatory patient. A lengthy air hose coupled the air pump and motor disposed in the recorder housing to the air bladder disposed within the arm band which is snugly wrapped around the patient's upper arm and held fast in position by Velcro attachment means. The housing also holds the system a battery as the system power supply. A microphone blood pressure auscultatory, Karotcoff sound sensor would be held in position by a piece of tape over a brachial artery of the patient just under the arm band. The microphone would then be coupled by a lengthy electrical lead to record blood pressure data on a magnetic tape cassette recorder in the recorder housing. The housing, worn on the patient's belt, also enclosed necessary electronics and a microprocessor to enable the device to periodically and on command receive and store a blood pressure and heart rate reading over an extended period of time. The housing also conventionally has mounted thereon an event marker tab, control tab and liquid crystal display, LCD. On taking a reading, the pump must pump a compressible volume of air along the lengthy air hose and into the air bladder to inflate the arm band and thereby tighten and necessarily cut off the flow of blood through the main artery of the arm. The microprocessor then allows air to bleed out the air bladder to lessen the grip of the arm band to obtain a systolic and subsequently a diastolic reading, normally in the range of 120/80, with a pulse rate normally around 60.

The invention disclosed herein satisfies a long felt need to provide for a long term, ambulatory blood pressure measurement and data recorder apparatus that is less bulky, less apparent to the eye and to the wearer when worn by a patient, that requires less energy to operate, which enables the monitor/recorder to run for a longer period, that can be mounted with one hand and where excess electrical leads and pneumatic pump tubes are all but eliminated by incorporation of the electrical power system (batteries), the pneumatic (air) pump system, microprocessor controller, digital system memory and digital data memory and electronics, and blood pressure transducer detector, all assimilated into a single package component housing and mounted on the blood pressure arm band.

Figure 1A:
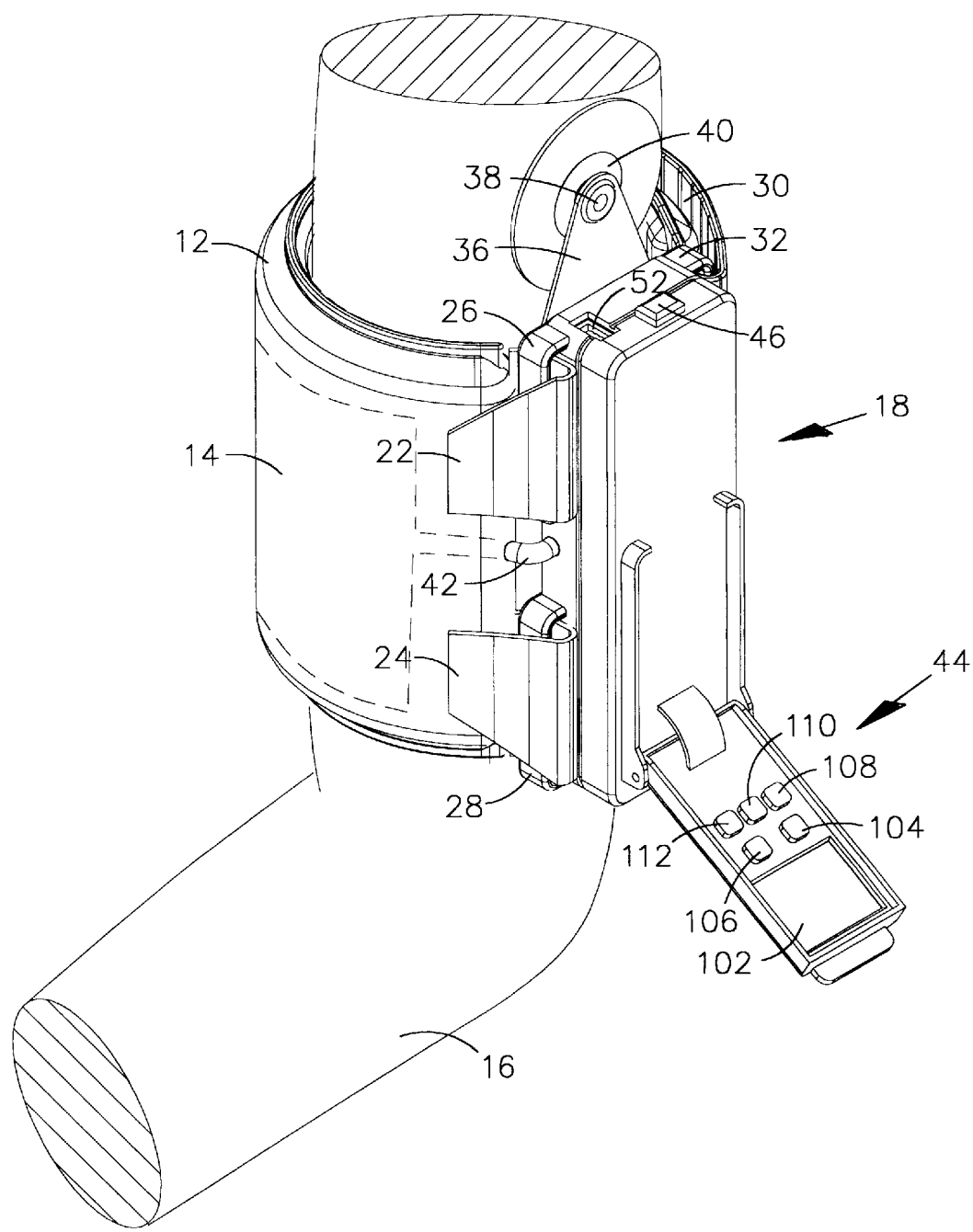
FIG. 1a illustrates a perspective view of the self contained ambulatory blood pressure cincture apparatus positioned on a patient's arm.
Figure 1B:
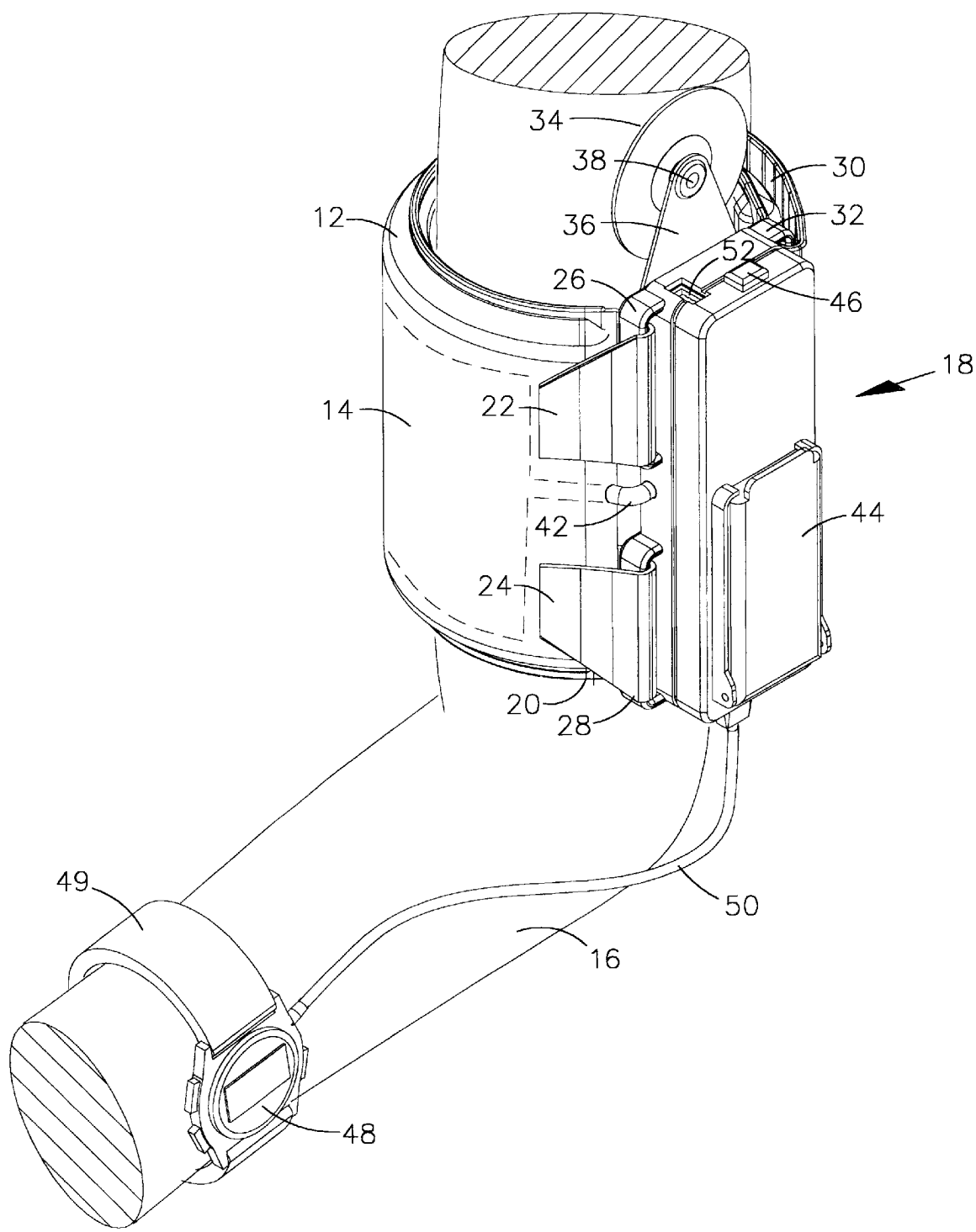
FIG. 1b illustrates an alternative embodiment of the invention that incorporates an additional control and display module on a wrist watch coupled to the cincture housing.
Figure 2:
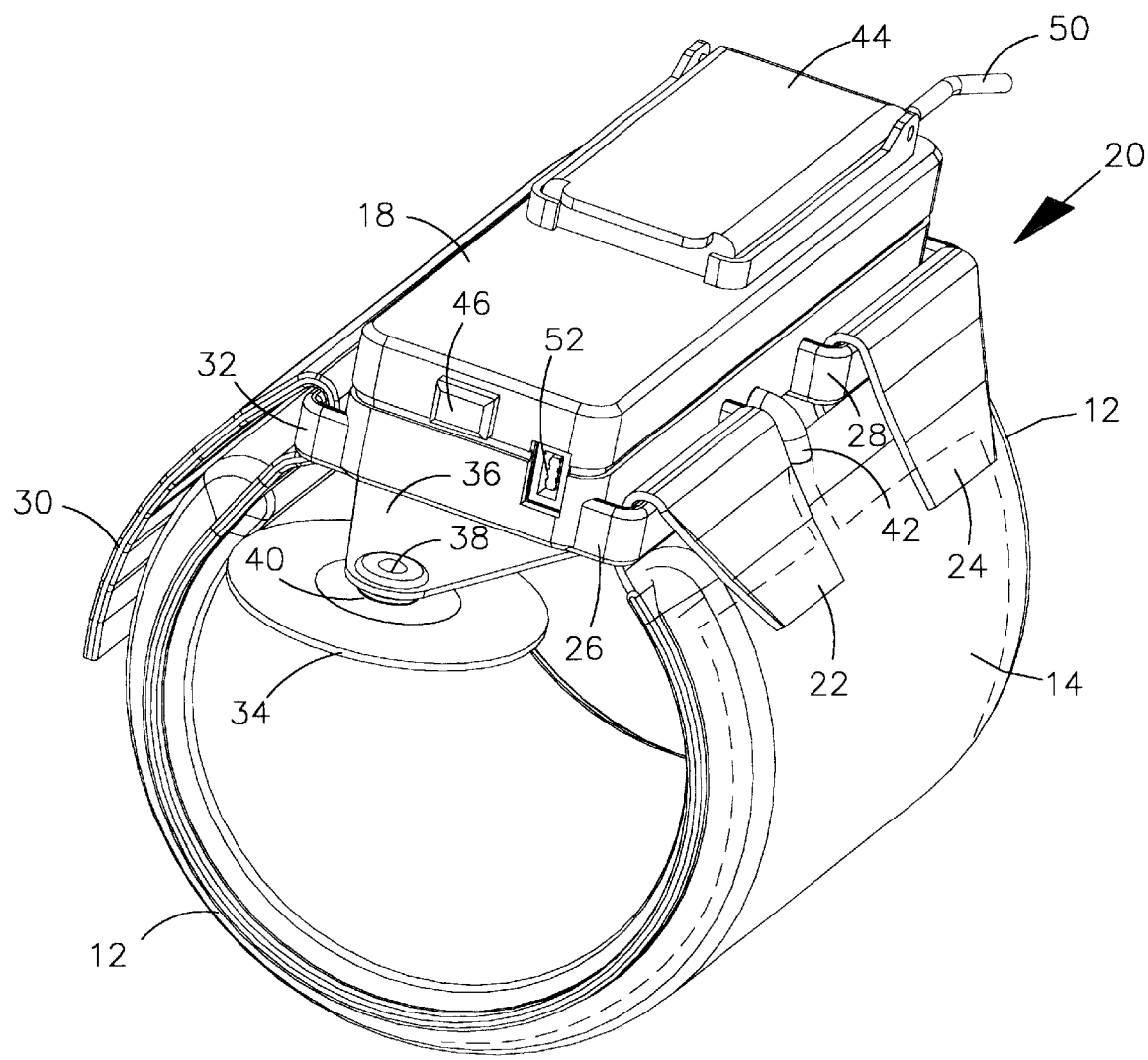
FIG. 2 illustrates a perspective view of the ambulatory blood pressure cincture housing and arm band apparatus alone.

Referring now to FIGS. 1 and 2, an overall view of a preferred embodiment of the invention is disclosed. In FIG. 1, a flexible arm band 12 having an inflatable air bladder 14 disposed therein, indicated by dashed lines, is placed around a patient's arm 16. Arm band 12 may consists of any flexible material, cloth, plastic, rubber; however, it is preferable that arm band 12 be more in the nature of cloth in order that the material surrounding the arm can let the skin breath. It is anticipated that long term ambulatory blood pressure monitoring may last for many hours. In such case, the arm band should not only hold the cincture housing in place but also allow the skin to breath, and also should be relatively light in weight so as not to further encumber and inconvenience the patient. Bladder 14 my likewise be of any flexible material, not limited to rubber or plastic, that can, of course, contain a volume of pressurized air.

A self contained arm band combination cincture coupler and component housing (cincture housing) 18 is firmly attached to a first end 20 of arm band 12 by a pair of lip extensions 22 and 24 which are looped around a pair of securing slot receptacles 26 and 28, respectively, of cincture coupler 18. The second end 30 of arm band 12 can conveniently be looped around a single slot extension 32 and removably secured to the top of arm band 12 by magnetic attachment means or Velcro type means by use of only one hand of the patient or physician. The Velcro attachment means of the prior art necessitated at least one other person or at least two hands to apply the arm band securely around a patient's upper arm. The invention described herein is designed to enable one to apply arm band 12 by one's self with only one hand. In particular, an adhesive mounting pad 34 is first attached to a patient's upper arm 16. A mounting extension 36 of cincture coupler 18 is provided with a snap on element 38 which can receive a mating snap in element 40. Mounting extension 36 is designed to suspend arm band 12 and cincture coupler 18 from the arm whilst second end 30 of arm band 12 is looped around and passed through slot extension 32 to secure and tighten up arm band 12 around the patient arm 16. Mounting extension 36 and adhesive mounting pad 34 also maintain cincture coupler 18 in a relatively fixed position on the patient's arm while in an ambulatory mode.

A pneumatic air hose 42 couples a pneumatic air pump in cincture coupler 18 to air bladder 14 in arm band 12. This shortened air hose element alone is a substantial step in novelty of the present invention. It should be noted that the prior art air hose was of necessity very long, streatching from the patient's belt line to the patient's upper arm. The unique design of the present invention has all but eliminated the air hose link between the pneumatic pump and motor and the inflatable air bladder 14 in arm band 12. The air hose of prior art equipment was of necessity several inches long; air hose 42 of the present invention is only in the realm of an inch or so in length.

Cincture coupler 18 is further provided with a choice of two display and control modules. A flip top display and control module 44 is molded into the exterior of coupler 18 and electrically directly coupled thereto. Module 44 may be easily accessed in a shirtless environment with a related event button 46 conveniently positioned on the top edge of coupler 18. In the event that the ambulatory blood pressure monitor is preferred to be used in a non obvious manner and hidden under clothing, an alternate wrist watch type display and control module 48 may be used, held in place by a flexible wrist band 50, and may be utilized concomitantly with or alternatively to flip top module 44. Wrist display and control module 48 is coupled to the bottom of coupler 18 by an electrical lead 52.

Once data is accumulated in memory in coupler 18, the data can then be downloaded to a PC or other data analysis device via a data outlet port 52 on the top end of coupler 18.

Figure 3:
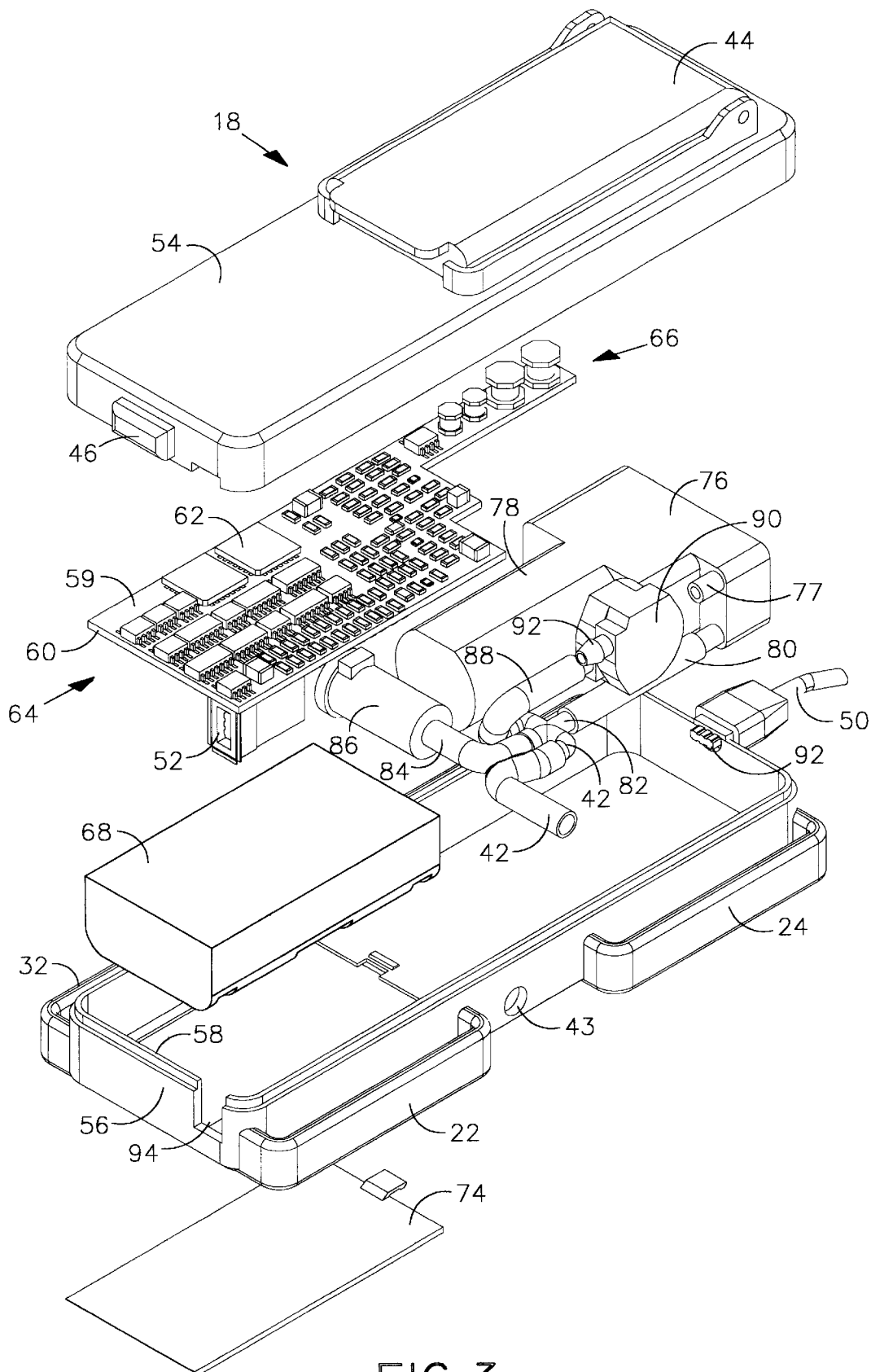
FIG. 3 illustrates a topside perspective exploded view of the cincture housing and internal components thereof.
Figure 4:
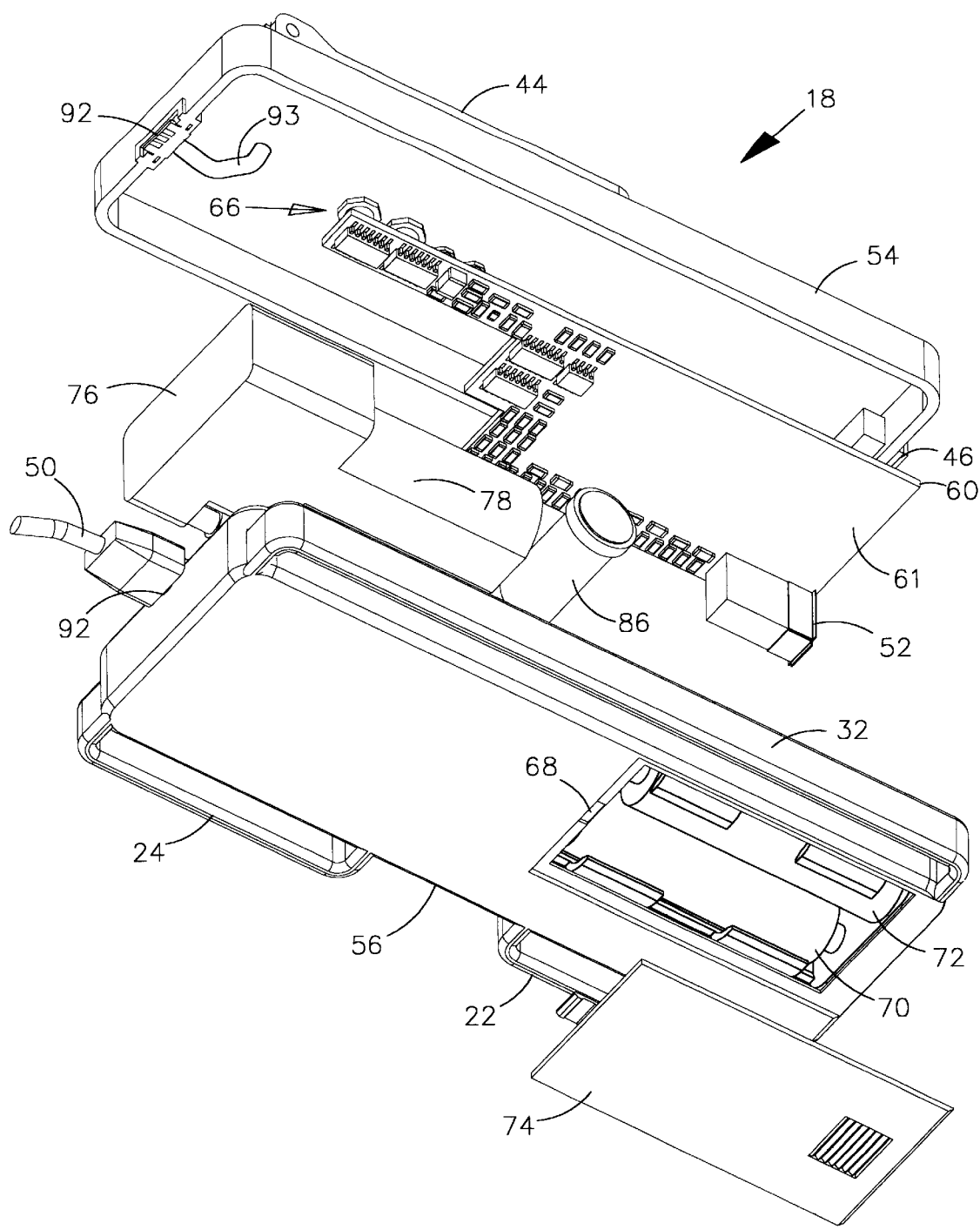
FIG. 4 illustrates an underside perspective exploded view of the cincture housing and internal components thereof.

Referring now to the exploded views of cincture coupler 18 in FIGS. 3 and 4, an explanation of the contents of cincture coupler 18 will be delineated. Coupler 18 consists of a two rectangular encasements, an exterior shell 54 and an interior shell 56, that snap snuggly together along a peripheral retaining rim 58. Shells 54 and 56 are preferably molded from any light weight but strong polymer, plastic or Santoprene (trademark of Advanced Elastomer Systems) rubber compound to fit comfortably on a patient's arm. The flip top display and control module 44 is molded as a contiguous component of exterior shell 54 as would be event switch 46. A two sided system printed circuit board PCB 60 having a top side 59 and underside 61, is snuggly mounted within exterior shell 54. PCB 60 holds, among other components, a system control microprocessor 62, EEPROM non volatile data memory chips 64, voltage coils 66, analog to digital, A/D, converters, amplifiers, diodes, resistors, etc., more clearly delineated in the schematics disclosed herein. A battery compartment 68 is mounted below PCB 60 and snuggly holds two AA batteries 70 and 72 within a battery compartment door 74. A pneumatic pump station 61 and motor 78 are also contained within cincture coupler 18. Pneumatic pump 76 is provided with an air inlet port 77 and an air outlet tube 80 that terminates in a three way split air manifold 82: a first split off 42 passes air from pump 76 through a hole 43 to air bladder 14; a second split off is passed to a manifold shut off solenoid 86. Solenoid 86 is configured to shut off air flow through manifold 82 when sufficient air pressure has been reached in air bladder 14. A third split off 88 passes air to an air pressure sensor 90 that functions as a blood pressure sensor and uses the "oscillatory method" as opposed to the "auscultatory method" of prior art to detect variations in blood pressure, and thereby determine the required systolic/diastolic blood pressure readings. Pressure sensor 90 is further provided with and air inlet/outlet valve 92 for access to ambient air pressure.

It can be observed from FIGS. 3 and 4 that interior shell 56 of cincture coupler 18 is provided with an input port 92 for the wrist watch display and control module 48. Input port 92 is coupled by cable 93 to flip top display and control module 44 and is, of course, coupled to PCB 60 by cable, not shown, in similar manner as is event switch 46 disposed in exterior shell 54. Shell 56 is also provided with a data output port 52 mounted directly on PCB 60 and is configured to fit snugly within an output port slot 94.

Figure 5:
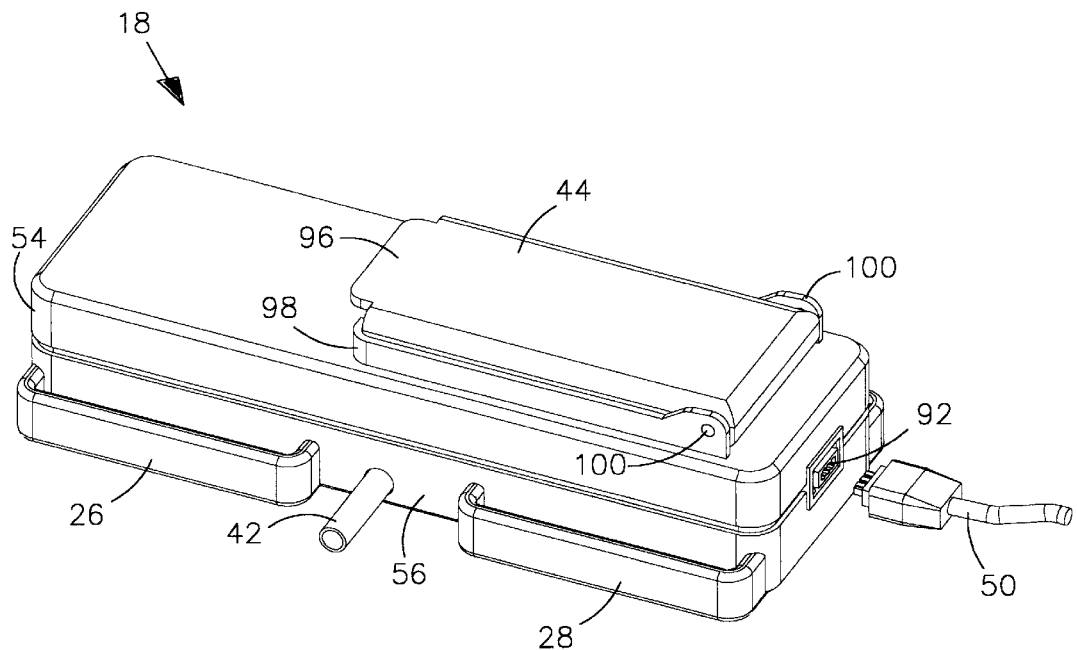
FIG. 5 illustrates a perspective view of an isolated cincture housing with the flip top control/display module in a closed position.
Figure 6:
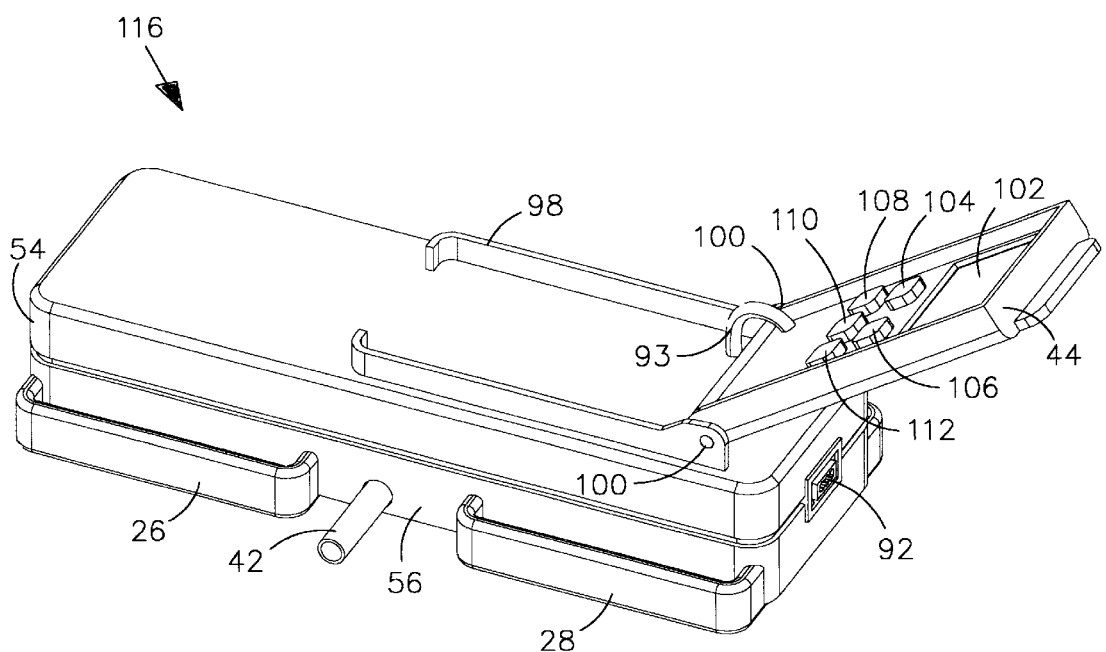
FIG. 6 illustrates a perspective view of an isolated cincture housing with the flip top control/display module in an open position.

Referring now to FIGS. 5 and 6, the combined cincture coupler and component housing 18 is depicted to more clearly illustrate the unique flip top display and control module 44. FIG. 5, of course, indicates the flip top module 44 in closed position and FIG. 6 illustrates the open position. Module 44 consists of a door 96 that snugly snaps into a support frame 98. Door 96 is provided with spring hinges to revolve about an axle 100 and is coupled to input 92 by a flexible lead/bus 93. Flip top module 44 carries a liquid crystal display LCD 102 for input and output of data programming functions and a plurality of switches/buttons on a keyboard 103 for operation and control of the blood pressure monitor, consisting of, but not limited to, the following: on/off 104, start 106, protocol 108, illumination/light 110, and cancel 112. Recall that the event button 46 for the flip top access is positioned on the top edge of cincture coupler housing 18.

Figure 7:
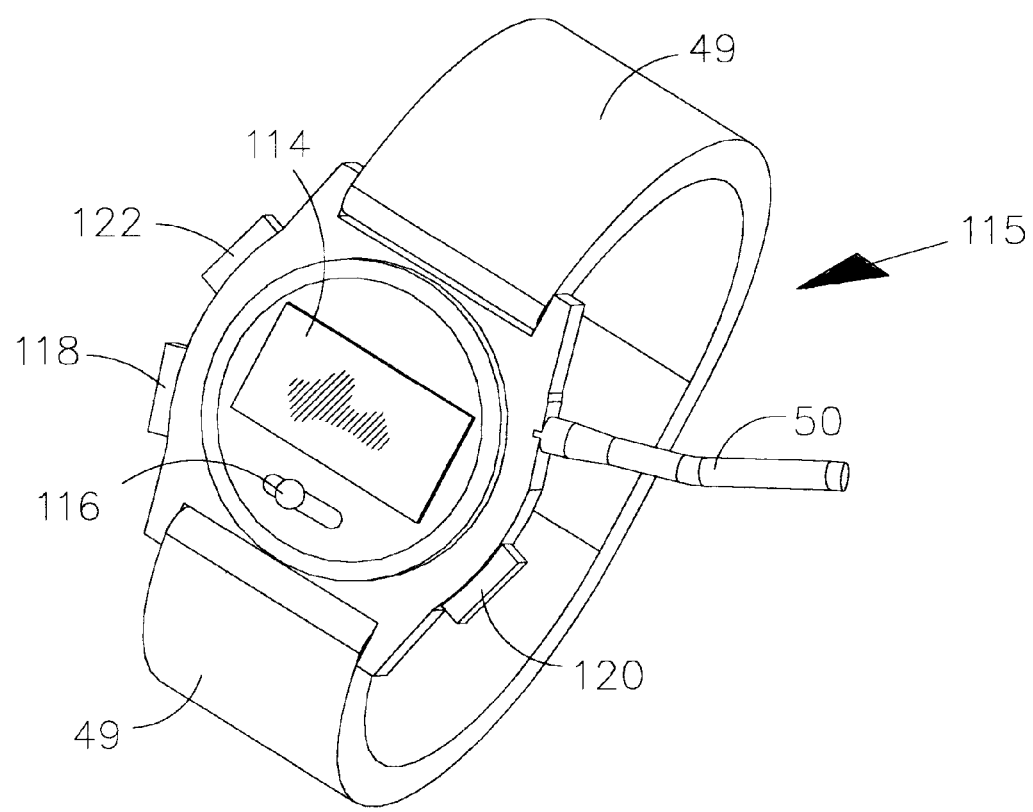
FIG. 7 illustrates a plan view of the wrist watch control/display module.

The wrist watch display and control module 48 is more clearly delineated in FIG. 7, where an alternative LCD 114 is evidenced and a similar series of function/control keys/pads/buttons comprising a keyboard 115 are implemented as follows: on/off 116, start 118, protocol 120, and event 122.

It should be understood that the foregoing function buttons are not limited to those indicated herein, but may include the above or entirely different function buttons without diverting from the concept of the invention. The function buttons, however, as presently conceived, are delineated as follows.

The "light" button is self explanatory. When the light button is depressed, the LCD and keys/buttons are illuminated for ease in viewing the panel at night and in areas lacking illumination.

The "on/off" button turns the monitor/recorder on and off; no data is lost when the device is turned off. This button should only be operated by the attending physician.

The "protocol" button allows the physician to choose between various software versions that will control and direct the system microprocessor. After having selected a protocol in the software, one must ensure that the corresponding protocol on the recorder has been selected. This is done by repeatedly pressing the protocol button until the desired protocol appears on the LCD, A protocol can only be changed when the memory is empty. Usually general practitioner physicians have a standard protocol defined in a first protocol and use a second or third protocol when they wish to change interval times, i.e. when the arm band is to be pumped up to take a blood pressure reading, or measurement frequencies.

A "day/night" button, not illustrated in the preferred embodiment, but if used, allows a more accurate, individual evaluation by clearly defining the awake and asleep phases of the patient. Both the norm values and the frequency of the measurements are adapted to the day and night rhythms. The patient can press this button within a four hour time frame; i.e. if the night interval is programmed to begin at midnight, the patient can activate the button between 8:00 pm and midnight. The button will beep when pressed. It can only be activated once within a four hour time frame. The same principle holds for the morning time frame as well. If the patient forgets to press the "day/night" button, the monitor will follow the pre-defined measurement cycle. The physician should check this item. Day and Night will appear on the printed protocol under comments.

The "event" button serves as a marker. By pressing the event button the display will show "E—E". The event button does not normally start an additional measurement, it merely marks the time in the print out together with the comment "event"; however, it should be apparent that the monitor soft ware/firm ware can easily be changed to accommodate a measurement every time the event button is depressed. Ideally, a patient should press the event button on significant occasions, such as every time medication is taken; however, if symptoms are felt, the event button can and should also be pressed, followed by the start button, in order to have an additional manual measurement. The patient should be encouraged to keep an event diary, and note down the reasons for pressing the event button.

The "start" button has two functions: to initiate beginning measurements and to initiate extra measurements. "Beginning measurements", the blood pressure monitoring process starts by pressing the start button. A manual measurement will begin immediately, allowing the physician to check that the device is working properly, that the cuff is correctly fitted and that the patient keeps his or her arm sufficiently still. If this manual measurement is successful, the patient can leave with confidence. To be safe it is better to wait for the first automatic measurement, usually every 15 minutes. "Extra measurements", the start button also allows the patient to initiate a manual measurement at any time he/she thinks fit; i.e. when the patient feels ill or stressed or excited. The patient should make a note in hil/ner event diary on why the button was pressed. When the button is pressed a number will appear shortly on the LCD denoting the amount of measurements up to that point. Directly afterwards the monitor will begin inflating the cuff. The extra measurements will be marked "manual" in the print out.

By mounting the LCD 61 and function control buttons/switches in a "wrist watch" manner on the patient's wrist, the patient can very conveniently and inconspicuously tap the event button at any noteworthy time, i.e. at a period of high physical activity, at a time when the patient may experience some heart discomfort or pain, at a time when under stress, at a time when taking medication, etc. The event button would then put a "flag" and a "time" on that portion of the recorded data in solid state "flash" memory to be given "special" attention on analysis of the recorded data in light of the "event."

Also by mounting the LCD and function control button on the patient's wrist, the patient can very conveniently and inconspicuously, as desired, tap the "start" button that will commence the inflation process and take a blood pressure and pulse rate measurement which will be recorded in memory at that time and concomitantly displayed on the LCD. It is more than likely and suggested that both the event button and the start button would be tapped together to note why the reading was taken by the patient in relation to the event.

It can be observed that the wrist watch display and control module 48 may, but need not, be coupled to coupler 18 through input port 92 by lead 50 dependant on need and convenience. It is envisioned that the wrist display and control module is wired in parallel with the flip top display and control module as a convenient redundancy to each other; i.e. what appears on one display screen will likewise appear on the other, and what function keys are depressed on one will so operate with the other module, unless the alternate module is turned off. When a patient is wearing the monitor in a relatively shirtless/coatless environment, it might be more convenient for patient and physician to disconnect the wrist watch module 48 and rely only on use of the flip top module 44. Alternatively, when the patient is wearing the monitor under clothing that would be too inconvenient to take off to view and operate the flip top module 44, then the patient could plug in and wear the wrist watch module to secretly and conveniently view and operate the blood pressure monitor status on his wrist.

Figure 8:
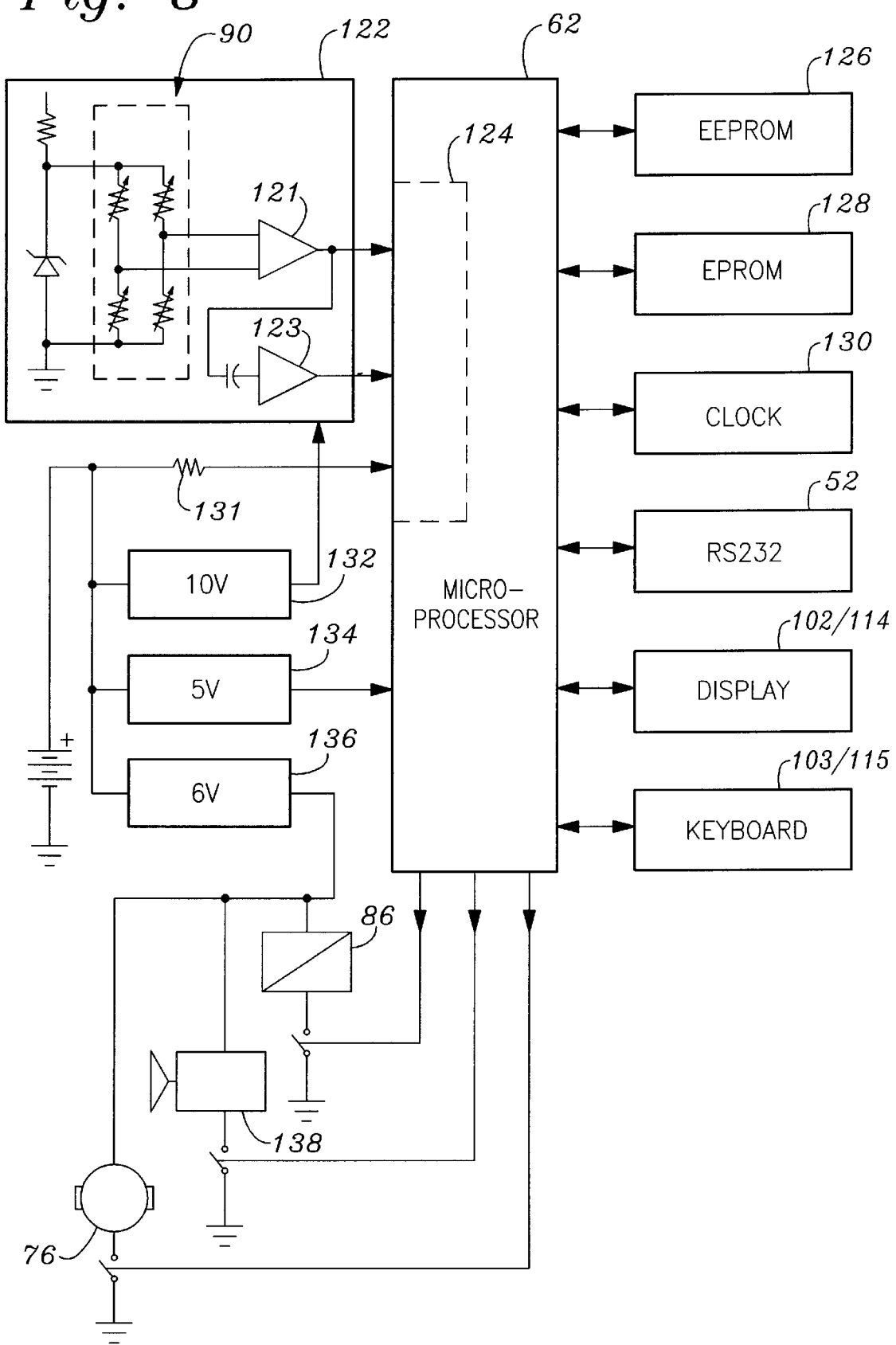
FIG. 8 delineates a block flow diagram of the system controller circuit.
Figure 9A:
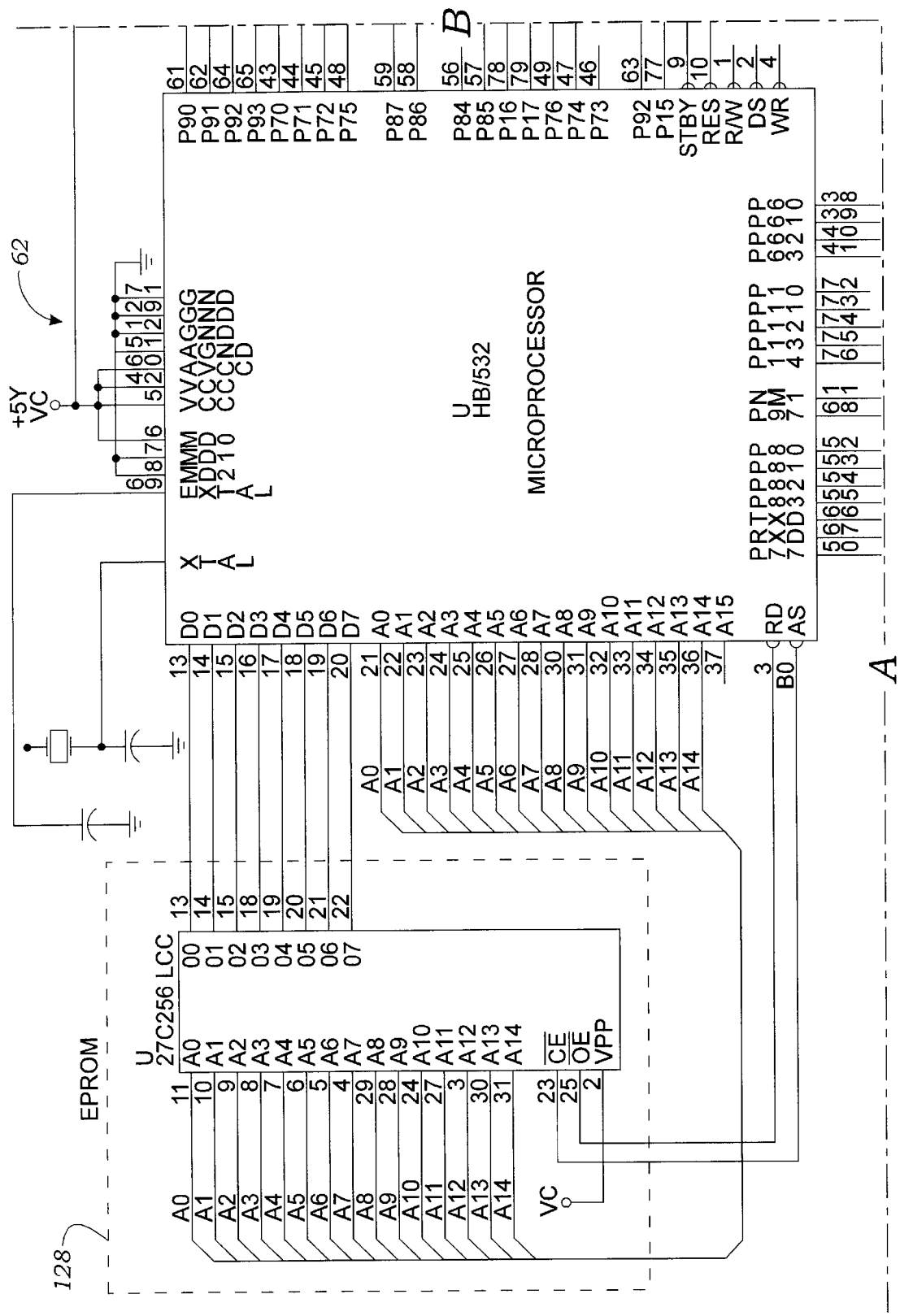
FIG. 9 delineates a detailed electronic schematic of the microprocessor system controller circuit.
Figure 9B:
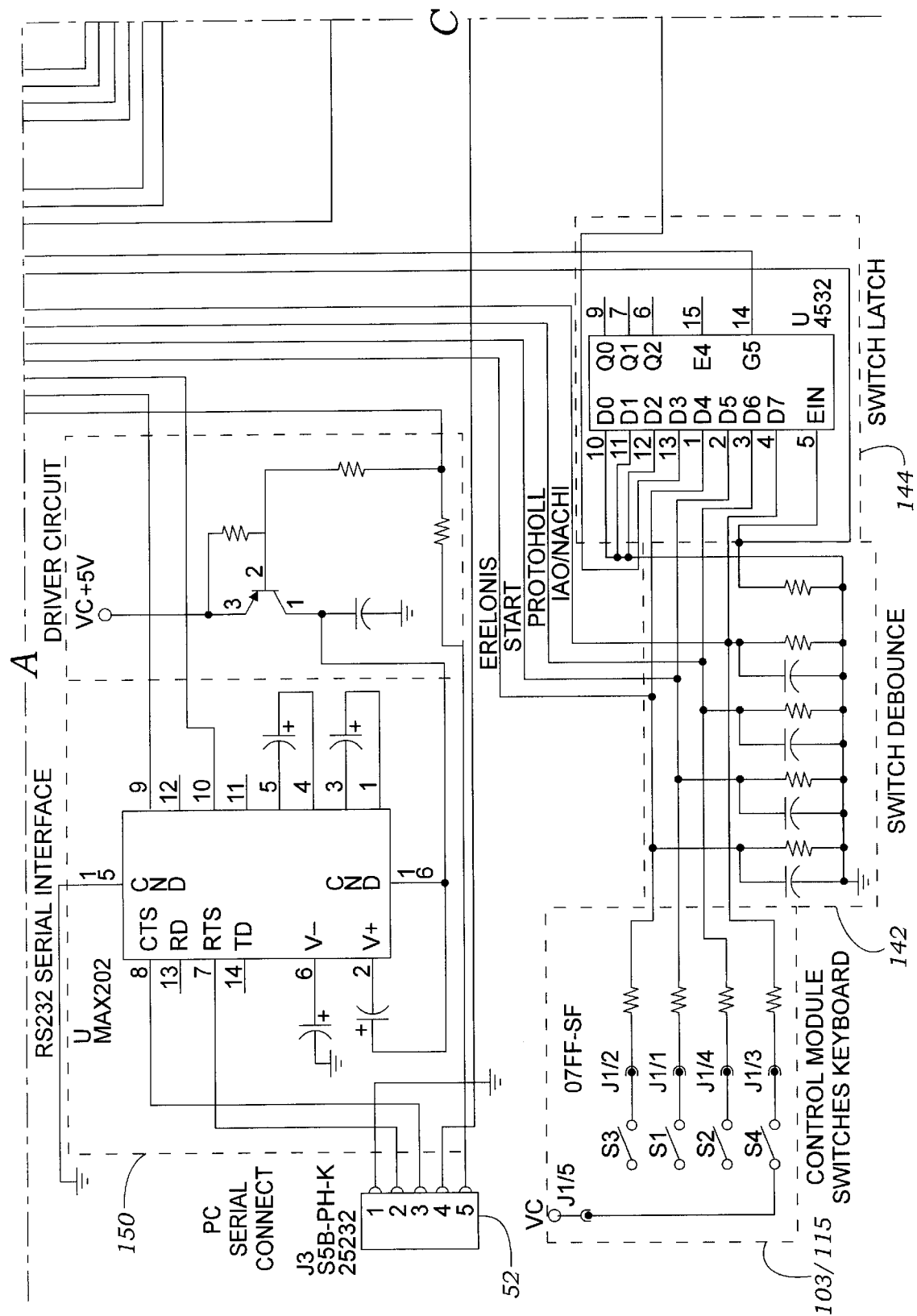
Figure 9C:
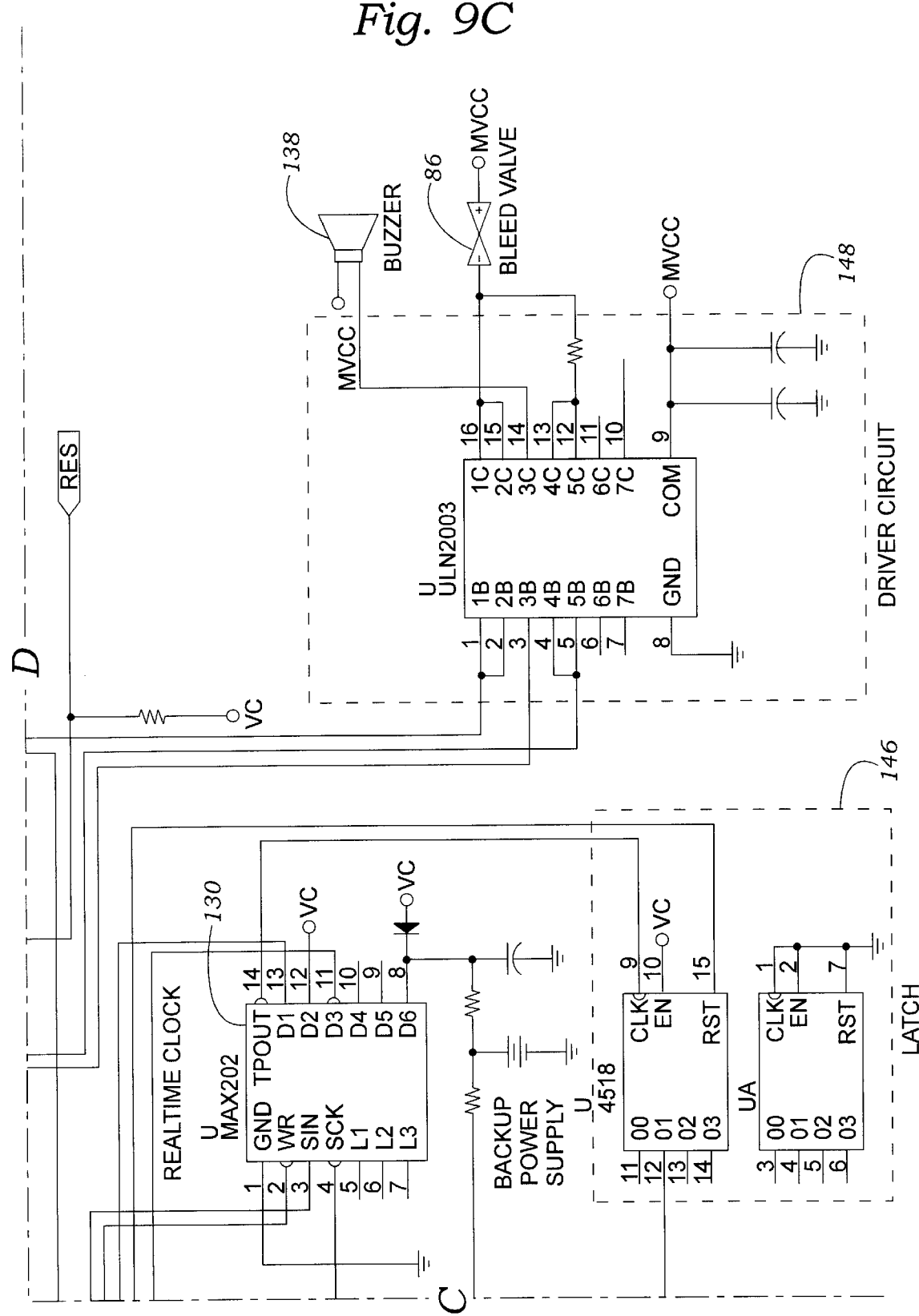
Figure 9D:
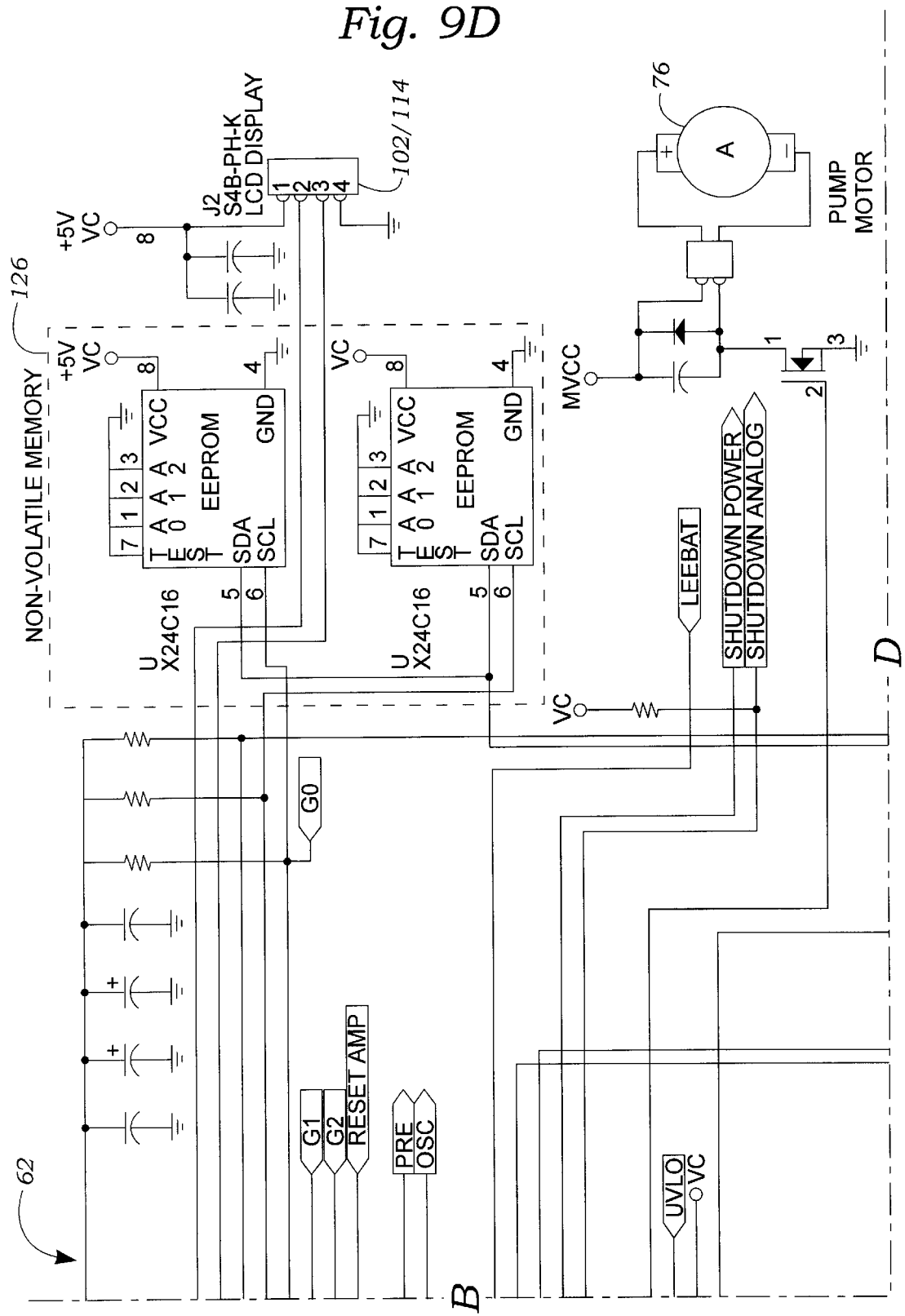

A block flow diagram of the blood pressure system functional components illustrated in FIG. 8 will more clearly explain and give an overall view of the system operation. On periodic command from microprocessor 62, or on election of the patient by pushing the "start" button 118, pneumatic motor and pump 76 is enabled to pump air into bladder 14 in arm band 12 through air hose 42 with solenoid valve 86 in the normally open position. At a predetermined air pressure sensed by sensor 90, all blood flow through the brachial artery is stopped, at which point air is permitted to bleed out of bladder 14 through valve 92 of sensor 90. Under the "oscillatory" method, micro processor 62 monitors the pressure ratings as they occur in bladder 14 through sensor 90 in a series of brief pressure oscillations of increasing amplitude up to a maximum amplitude and then decreasing oscillation amplitudes. The envelope of this series of data would then lead to an envelope of data elements from which a "mean average pressure" MAP could be determined. Alternatively, the MAP could be determined by formula: $P_M=P_S+(\frac{1}{3})(P_D-P_S)$ where $P_M$ is the MAP, $P_S$ is systolic blood pressure and $P_D$ is diastolic blood pressure. In either event, systolic and diastolic blood pressure can be determined according to: $P_S=(0.4) P_M$ and $P_D=(0.6) P_M$.

In the block flow diagram of FIG. 8, a sensor block 122 consists of oscillometric sensor 90 the output of which is passed through an instrumentation amplifier 119 and a pulse amplifier 123. The analog pulse is passed to an analog to digital converter 124 to be operated upon by microprocessor 62. Data on blood pressure/rate readings from sensor block 122 is stored in an electronically erasable programmable read only memory, EEPROM block 126. Temporary blood pressure non volatile data storage in EEPROM 126 is, of course, protected from system shut down and other contingencies, e.g. due to lose of power, but can conveniently be expunged at will. Data stored in EPROM block 128 consists of the system operation program codes and is of a more fixed and permanent nature; if desired a reprogrammed EPROM could easily inserted to change the system operation. A real time clock 130 provides the intricate timing circuit necessary to operate on microprocessor 62 to receive, classify, document and record data from sensor block 122. A serial output, RS232, data output 52 permits recorded data accumulated over a period of time, generally a 24 hour period, to be directly input to a personal computer, PC, or other data analysis device. The programming functions, system operation and modes, and data are visually displayed in flip top block 102 and wrist watch block 114 as described earlier. The flip top keyboard 103 and wrist watch keyboard 115 block provide access to program microprocessor in the appropriate mode and, of course, to activate the monitor as discussed infra.

It is necessary that the system be provided with at least three different power levels. Therefor a voltage power circuit is incorporated in PCB 60 as well to yield a DC 10 volt power source 132 to power the sensor device block 122, a 5 volt power source 134 to power the digital circuits and microprocessor 62, and a 6 volt power source 136 to power the DC pneumatic pump motor 76, a buzzer circuit 138 that can indicate various monitor functions, and pneumatic air release valve 86. Resister element 131 simply to sets all power sources at the same base and thereby enables microprocessor 162 to adequately monitor all three power sources.

Figure 10A:
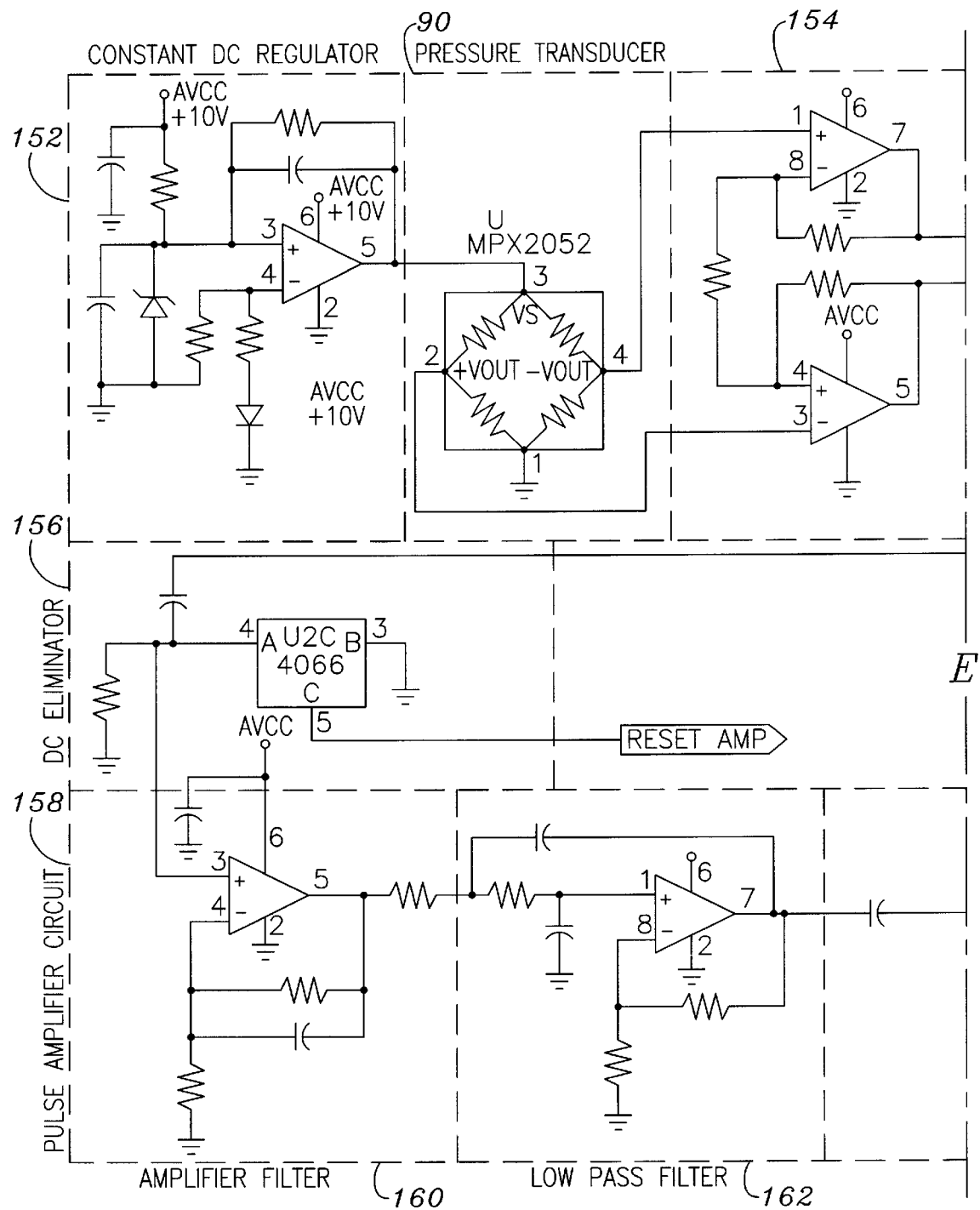
FIG. 10 delineates a detailed electronic schematic of the blood pressure sensor transducer circuit.
Figure 10B:
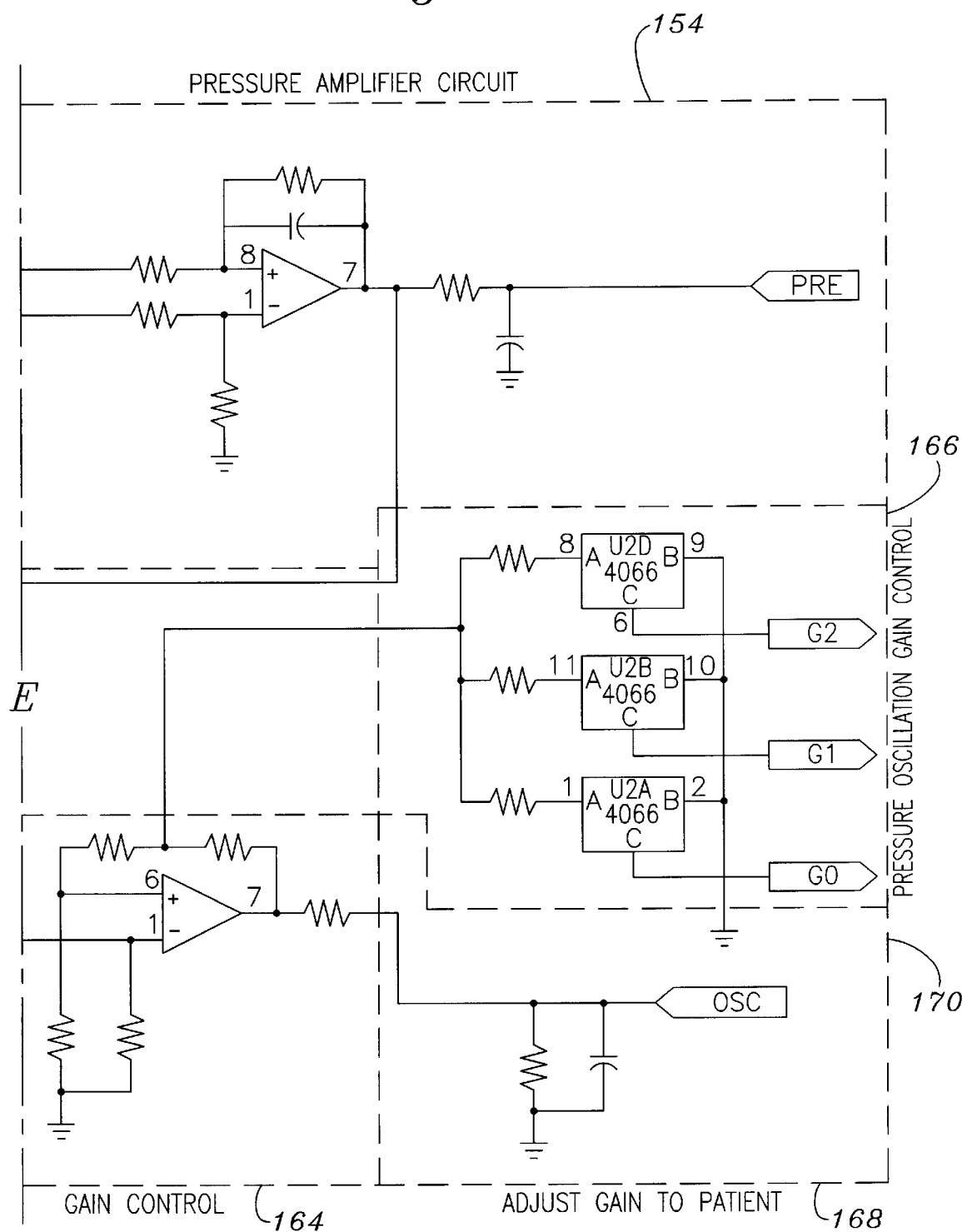
Figure 11A:
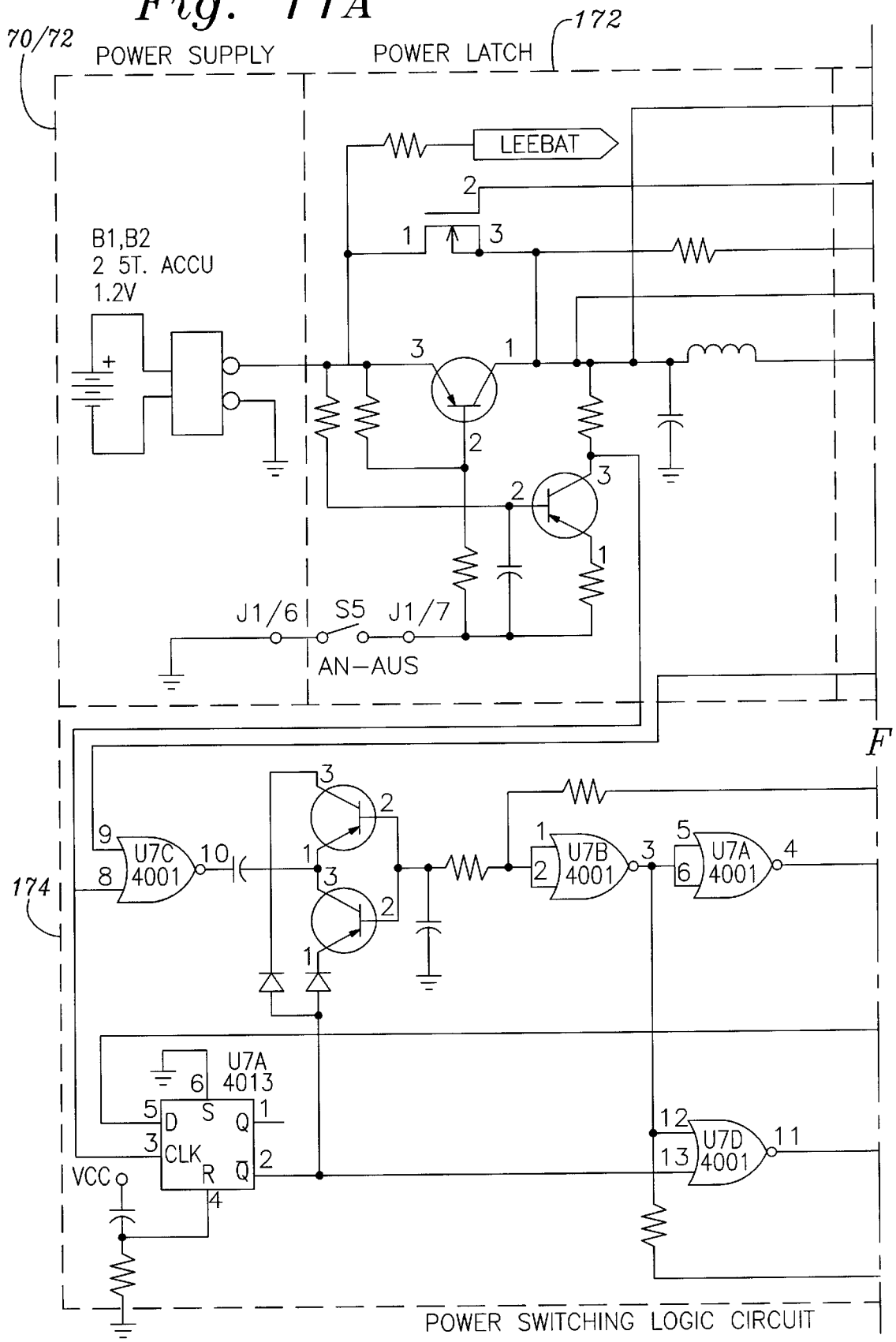
FIG. 11 delineates a detailed electronic schematic of the power supply circuit for generating the necessary three power levels.
Figure 11B:
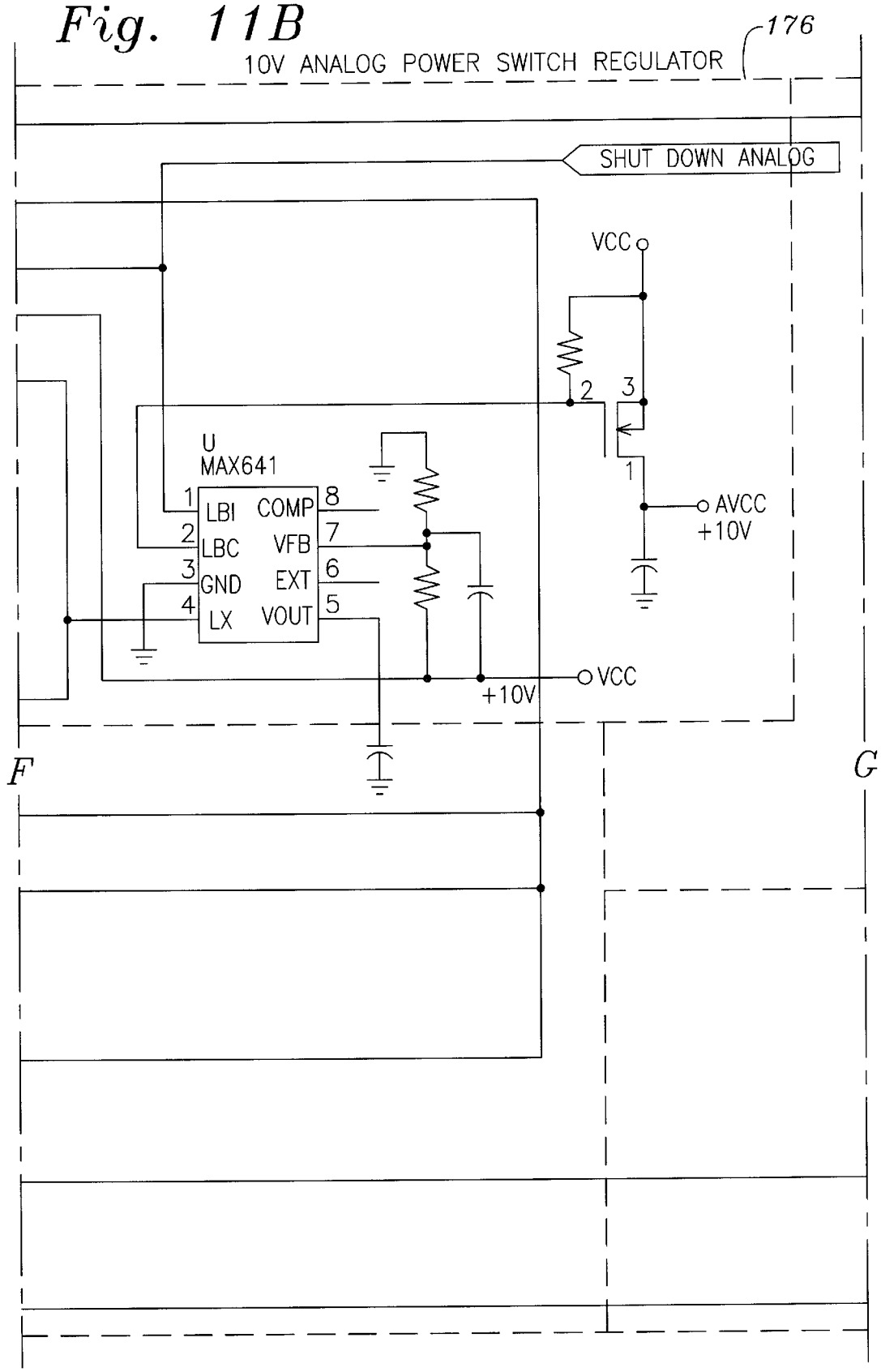
Figure 11C:
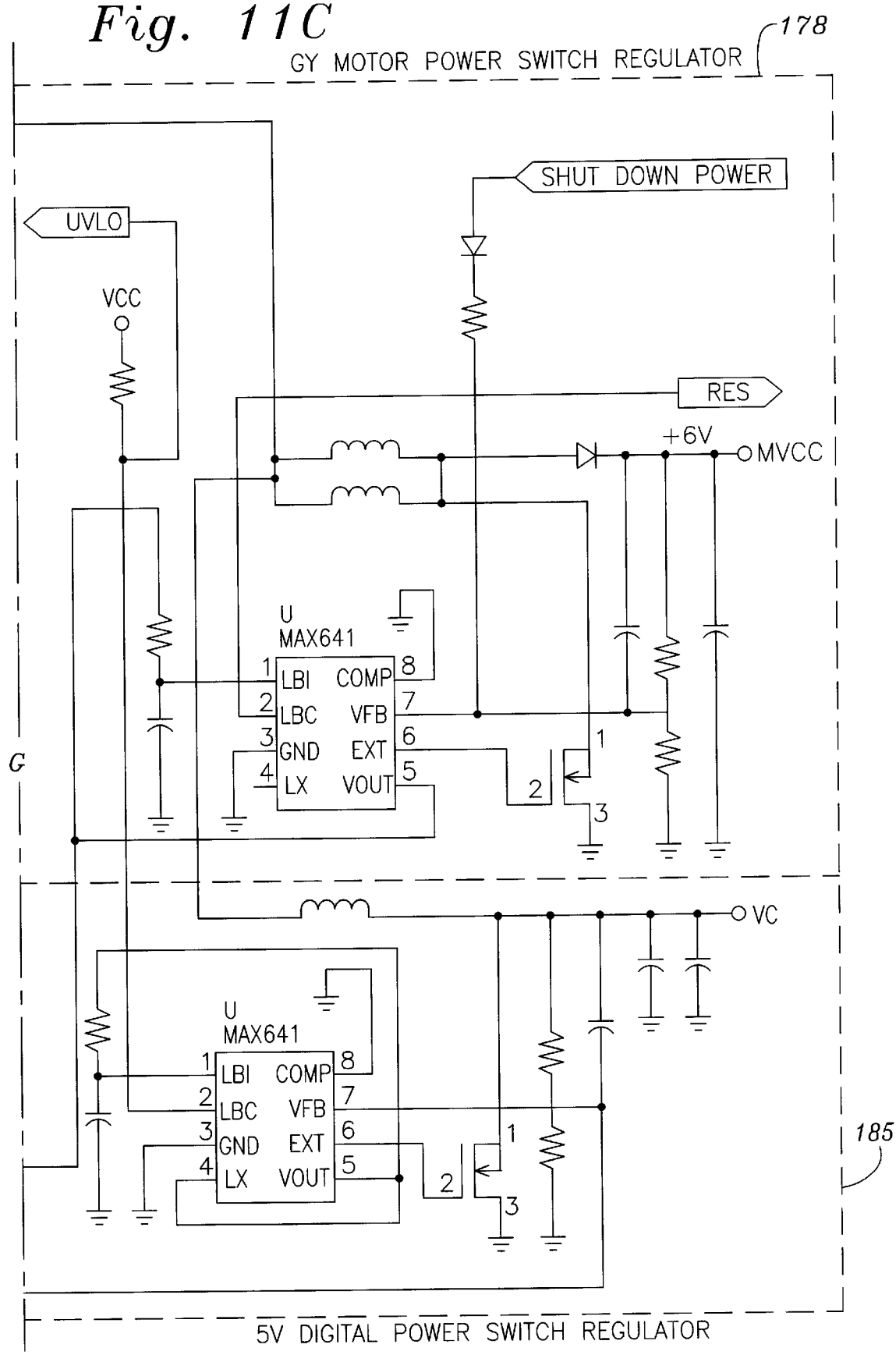

The electrical schematics of FIGS. 9, 10, and 11 provide a very detailed explanation of the circuits that are necessary to operate the invention. Applicant does not claim any proprietary interest or novel nature to said schematics; however, each is delineated herein to effect a full and complete disclosure of an enabling embodiment of the invention as required. FIG. 9 delineates the basic blood pressure monitoring circuit. Control module switch/keyboard 103/115 input is smoothed out by a debounce circuit 142 before being passed to latch circuits 144 and 146 and thence to microprocessor 62 for storage of digitized data in non volatile memory, EEPROM, 26. The LCD, displays, 102 and 114, as well as pneumatic pump motor circuit 76 are coupled to microprocessor 62 in the manner indicated as is the buzzer 138 and bleed valve 86 driver circuit 148. Real time clock 130 regulates the processing of EPROM 128 coded programs and data accumulation. An RS232 serial interface driver circuit 150 enables accumulated blood pressure data in nonvolatile memory, EEPROM, 126 to be downloaded via output terminal 52. The microprocessor system program is initially set up by encoding elements in EPROM 128 as needed according to predetermined parameters as established by the manufacturer or physician.

Referring now to the pressure transducer circuit of FIG. 10, a constant DC regulator circuit 152 is applied to pressure transducer 90, the variable output of which is amplified by circuit 154 coupled by a DC eliminator circuit 156 to a pulse amplifier circuit 158, consisting of a amplifierifilter 160, a low pass filter 162, a gain control circuit 164, modified by a pressure oscillation gain control circuit 166, and patient gain adjustment 168 to yield an oscillametric output 170.

The third schematic of FIG. 11 delineates the triple output of the power supply circuit. The battery pack power supply, two M batteries, 70 and 72, is initially passed through a power on latch 172 and through a switching power logic circuit 174. Thereafter, an analog power switch regulator circuit 176 yields a 10 volt output, a motor power switch regulator circuit 178 yields a 6 volt output, and a digital power switch regulator circuit 180 yields a 5 volt out put for the microprocessor and digital circuits.

While the present invention has been disclosed and described with reference to the foregoing detailed description of a preferred embodiment, it will be apparent to those skilled in the art that other changes in form and detail may be made therein without departing from the spirit and scope of the invention as defined in the appended claims.

What is claimed as novel is:

1. An ambulatory blood pressure monitor, comprising:

inflatable arm band means for constricting blood flow through an artery;

cincture means disposed on said inflatbte arm band means, for not only securing said arm band means but also for housing all monitor components;

microprocessor means, disposed in said housing means, for controlling all monitor functions;

battery pack means, disposed in said housing means, for providing power;

pneumatic pump means, disposed in said housing means, for systematically inflating and deflating said arm band to initially constrict blood flow and subsequently slowly allow blood to freely flow to enable blood pressure variations to be assessed in the process;

memory means, disposed in said housing, for accumulating blood pressure data;

means, disposed in said housing, for sensing blood pressure variations and indications as artery constriction is released; and means, directly attached to and remotely attached to said housing, for displaying and controlling system functions.

\* \* \* \* \*